United States Patent [19]

Lepie

[11] Patent Number: 5,582,605
[45] Date of Patent: Dec. 10, 1996

[54] DISPOSABLE DIAPER ADAPTED TO CARRY TOILETRIES AND SANITARY ACCESSORIES

[76] Inventor: Eric J. Lepie, 2717 N. Magnolia, Tucson, Ariz. 85712

[21] Appl. No.: 270,597

[22] Filed: Jul. 5, 1994

[51] Int. Cl.[6] .............................. A61F 13/15; A61B 17/06
[52] U.S. Cl. .................. 604/385.1; 604/358; 206/438
[58] Field of Search ......................... 604/385.1–387, 604/389–396; 206/438–440

[56] References Cited

U.S. PATENT DOCUMENTS

| | | | |
|---|---|---|---|
| 4,221,221 | 9/1980 | Ehrlich | 604/385.1 |
| 4,702,378 | 10/1987 | Finckel et al. | 604/400 |
| 4,743,240 | 5/1988 | Powell | 604/385.1 |
| 4,931,052 | 6/1990 | Feldman | 604/385.1 |
| 5,304,158 | 4/1994 | Webb | 604/385.1 |

Primary Examiner—Randall L. Green
Assistant Examiner—K. M. Reichle
Attorney, Agent, or Firm—Victor Flores

[57] ABSTRACT

A disposable diaper structure that maintains the disposable diaper characteristics, but that is further adapted to include in its structure, detachable diaper change accessories. The diaper structure is provided with a compartment structure for storing a disposable pad for laying a child on during a diaper change and avoid exposing the child to an unsanitary surface during a change of diapers, and also provided with a plurality of other detachable accessories. The other accessories, may include washing towels, and toiletries, such as baby powders, lotions, and a sealable trash bag for disposal of all soiled and used items and their packaging material. The disposable convenience associated with the modern diaper is maintained, but further avoids a form of pollution of the environment in that dirty, soiled diapers can be sanitarily disposed of in public trash containers.

5 Claims, 1 Drawing Sheet

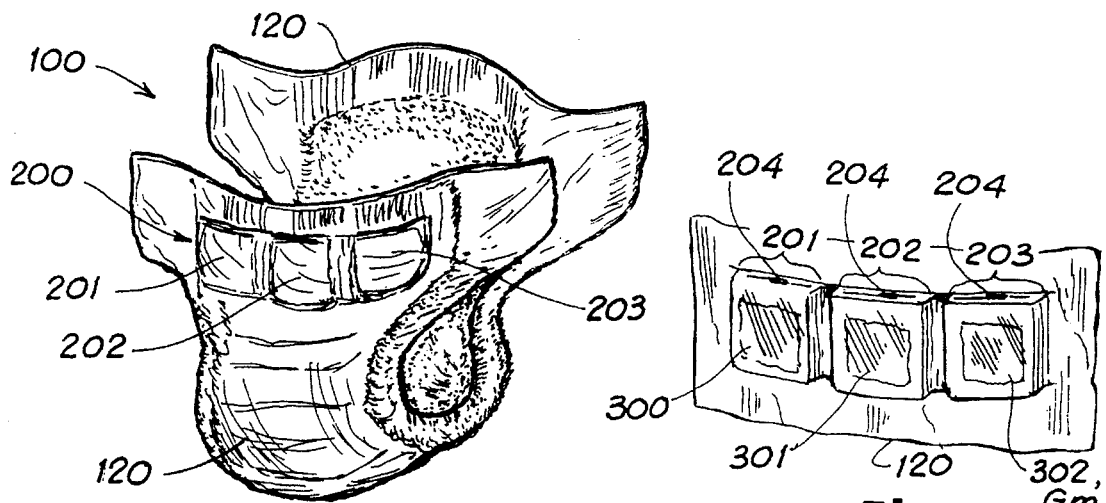
Fig. 1
Fig. 2
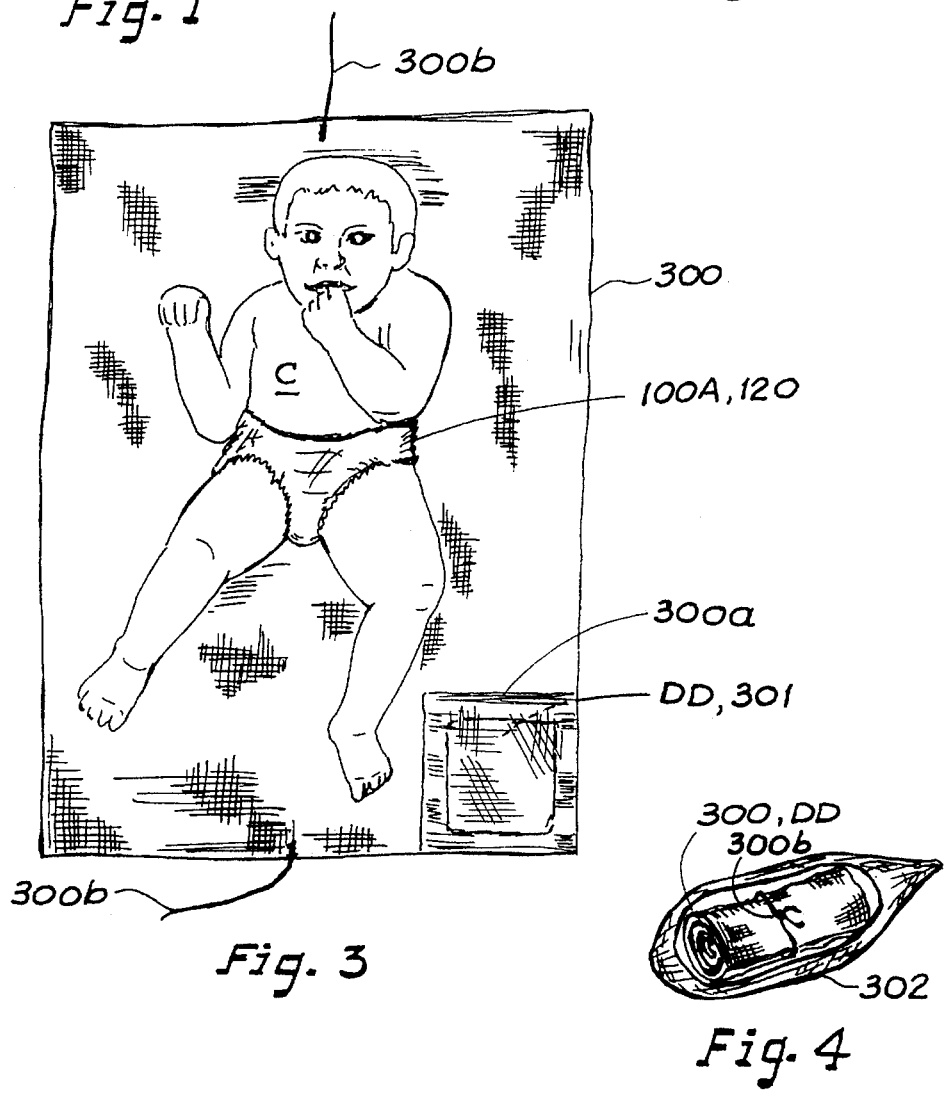
Fig. 3
Fig. 4

DISPOSABLE DIAPER ADAPTED TO CARRY TOILETRIES AND SANITARY ACCESSORIES

FIELD OF THE INVENTION

This invention relates to diapers. More particularly, the present invention relates to disposable diapers and accessories used to effect a sanitary change of a soiled diaper. Even more particularly, the present invention relates to integral diaper structures containing the diaper and accessories used to effect a sanitary change and subsequent disposal of a soiled diaper.

BACKGROUND OF THE INVENTION

Disposable diapers are a modern convenience which has found wide acceptance since their introduction by the diaper industry. The disposable nature of a disposable diaper has resulted in more freedom to travel by an individual user and those caring for the user. Unfortunately, the disposable convenience has also caused a form of pollution of the environment in that dirty, soiled diapers are readily found in public trash containers. The polluting situation is amplified primarily because the soiled disposable diaper, and any cleaning towels are not disposed of PROPERLY in a sealed individual container.

A further observation associated with the freedom of travel and the use of the disposable diaper is, that the individual user, for example a child, is exposed to an unsanitary surface during a change of diapers. A person caring for the child typically has a clean diaper, but does not have a pad to lay the child on to change the soiled diaper. If a pad is provided, it would be a separate item from the diaper, and would likely get soiled if used, and would be either disposed of, or carried around for subsequent washing. The net effect being that a child does not have a pad to lay on during a change of diaper situation. Towels, lotions and powders, and other toiletries, are also provided as separate items, typically in a diaper bag.

Thus, a need is seen to exist for a disposable diaper structure that maintains the disposable diaper characteristics, but that further provides structure, by example compartment structure, that includes a disposable pad for laying a child on during a diaper change, cleaning accessories, such as washing towels, and toiletries such as baby powders, lotions, and a sealable trash bag for disposal of all soiled and used items and their packaging material.

SUMMARY OF THE INVENTION

Accordingly, the primary object of the present invention is to provide a disposable diaper structure that maintains the disposable diaper characteristics, but that is further adapted to include in its structure, detachable diaper change accessories, including a surface pad, and a disposing bag means for the soiled diaper and related used accessories.

The foregoing objects are accomplished by providing a disposable diaper adapted with a plurality of accessories including at least one surface pad for laying on, at least one cleaning towel, an assortment of toiletry items, and a trash bag for disposing of all of the soiled articles.

Therefore, to the accomplishments of the foregoing objects, the invention consists of the foregoing features hereinafter fully described and particularly pointed out in the claims, the accompanying drawings and the following disclosure describing in detail the inventions such drawings and disclosure illustrating but one of the various ways in which the invention may be practiced.

BRIEF DESCRIPTION OF THE DRAWINGS

FIG. 1 is a perspective view of the present invention illustrating a disposable diaper adapted with compartments containing diaper changing accessories, such as a disposable surface pad, cleaning towels, and a trash bag.

FIG. 2 is a partial view of the disposable diaper illustrated in FIG. 1 further illustrating a cutaway of the compartments and the enclosed contents.

FIG. 3 is an applications view of the disposable diaper fitted on a child, illustrating the use of the disposable surface pad and other accessories removed from the compartments and utilization of a pocket on the pad for disposing of the soiled diaper.

FIG. 4 illustrates the disposable pad and included soiled diaper shown in cutaway view deposited in the trash bag for being disposed.

DESCRIPTION OF THE PREFERRED EMBODIMENT

FIG. 1 shows a disposable diaper structure 100 including a disposable diaper member 120 and a diaper changing accessory array 200, including, by example, a plurality of compartments 201, 202, and 203 for containing diaper changing accessories.

FIG. 2 shows a partial view of array 200 further illustrating the compartments 201, 202, and 203 provided with closure structure 204 for sanitarily enclosing the contents prior to use. By example, the contents in compartments 201, 202, and 203 would preferably include at least one surface pad 300 for laying a child on during the process of changing a soiled diaper, a toiletry item 301, such as a cleaning towel or baby powder, and a trash bag 302.

FIG. 3 shows the present invention a stage of utilization where a child C has had a change of diaper and is shown wearing the clean disposable diaper 120, depicted also as numeral 100A, which is effectively diaper structure 100 without the accessories. During a diaper change process, a person caring for child C would have diaper structure 100 available and would remove pad 300 from the array 200 and spread the pad on a surface in preparation for laying child C thereon for changing. By example, pad 300 is provided with a pocket 300a and a set of tie strings 300b. Pocket 300a is provided for enclosing soiled diaper DD and used toiletry items 301, such as cleaning towels, and used packaging trash material. Once the child has been changed, pad 300 is rolled up and tied using tie strings 300b. The rolled up soiled material is then further enclosed in the provided trash bag 302 as shown in FIG. 4 for proper and sanitary disposal. The accessories provided in array 200 preferably include a germicidal Gm that is user activated in trash bag 302 to counter offensive odor-causing bacteria and germs emitted by the discarded soiled diaper.

Therefore, while the present invention has been shown and described herein in what is believed to be the most practical and preferred embodiments, it is recognized that departures can be made therefore within the scope of the invention, which is therefore not to be limited to the details disclosed herein but is to be accorded the full scope of the claims so as to embrace any and all equivalent apparatus.

I claim:

1. A disposable diaper structure, said diaper structure comprising:

a disposable diaper member; and an array comprised of an arrangement of at least one compartment formed on said disposable diaper member for containing an assortment of detachable diaper changing accessories, said assortment of diaper changing accessories comprises at least one detachable pad for covering a surface and for laying a diaper user therein during a diaper change, and a trash bag for disposing of said pad and a soiled diaper removed from said diaper user during said diaper change.

2. A disposable diaper structure, as described in claim 1, wherein:

said at least one pad includes tie strings and at least one pocket portion for initially disposing said soiled diaper, said tie strings being used to secure said pad having said soiled diaper disposed in said pocket portion in a state for being sanitarily disposed.

3. A disposable diaper structure, as described in claim 1, wherein:

said assortment of diaper changing accessories comprises an assortment of toiletries, and a germicidal substance.

4. A method of disposing of a soiled diaper, said method comprising the steps of:

(a) providing a disposable diaper structure, said diaper structure comprising:

a disposable diaper member; and an array of diaper changing accessories detachably secured to said disposable diaper member, said accessories including at least one pad for covering a surface, and a trash bag, said at least one pad having a pocket member;

(b) providing a user wearing a soiled diaper;

(c) detaching said at least one pad and said trash bag from said array;

(d) spreading said pad on a surface;

(e) laying said user on said spread pad;

(f) removing said soiled diaper from said user and depositing it into said pocket member;

(g) putting said disposable diaper member on said user; and (h) depositing said spread pad having said soiled diaper in said pocket member into said detached trash bag for sanitarily disposing.

5. A disposable diaper structure, said diaper structure comprising:

a disposable diaper member; and an array comprised of an arrangement of at least one compartment formed on said disposable diaper member for containing an assortment of detachable diaper changing accessories, said assortment of diaper changing accessories comprises at least one detachable pad for covering a surface and for laying a diaper user thereon during a diaper change, and a trash bag, said at least one pad includes tie strings and at least one pocket portion for initially disposing said soiled diaper, said tie strings being used to secure said pad having said soiled diaper disposed in said pocket portion in a state for being sanitarily disposed within said trash bag.

* * * * *